United States Patent [19]

Zaehner et al.

[11] Patent Number: 4,996,156
[45] Date of Patent: Feb. 26, 1991

[54] PREPARATION OF SPORE-FREE, CONCENTRATED PROTEIN PREPARATIONS FROM *BACILLUS THURINGIENSIS* SEROVAR, *ISRAELENSIS*, WHICH IS TOXIC FOR GNATS, A MICROORGANISM FOR THEIR PREPARATION, AND THE ISOLATION OF THE MICROORGANISM

[76] Inventors: Hans Zaehner, 13 Im Hopfengarten; Konrad Bernhard, 132 Jessinger Hauptstrasse, both of 7400 Tuebingen; Harald Weisser, 80 Bruggerstrasse, 7210 Rottweil, all of Fed. Rep. of Germany

[21] Appl. No.: 22,830

[22] Filed: Mar. 6, 1987

[51] Int. Cl.$^5$ .................. C12R 1/07; C12P 21/00; A01N 63/00; C12N 15/01
[52] U.S. Cl. .................. 435/252.5; 424/93; 435/71.2; 435/172.1
[58] Field of Search ............ 435/252.5, 68, 71.2, 435/172.1; 424/93, 195.1

[56]  References Cited

U.S. PATENT DOCUMENTS 4,609,550 9/1986 Fitz-James et al. ............ 424/93

FOREIGN PATENT DOCUMENTS 99301 1/1984 European Pat. Off. .

OTHER PUBLICATIONS

Sastry et al., (1983) Jour. Bacterial. 153:511–519.

*Primary Examiner*—Charles F. Warren
*Assistant Examiner*—Barbara M. Chereskin
*Attorney, Agent, or Firm*—Keil & Weinkauf

[57] ABSTRACT

Asporous mutants of *Bacillus thuringiensis* serovar. israelensis, a process for their preparation and their use for the isolation of bacterial toxins for controlling diptera.

4 Claims, No Drawings

PREPARATION OF SPORE-FREE, CONCENTRATED PROTEIN PREPARATIONS FROM BACILLUS THURINGIENSIS SEROVAR, ISRAELENSIS, WHICH IS TOXIC FOR GNATS, A MICROORGANISM FOR THEIR PREPARATION, AND THE ISOLATION OF THE MICROORGANISM

Apart from synthetic insecticides and those obtained from higher plants, bacterial insecticides have been disclosed: various types of Bacillus thuringiensis, which has been known since 1915, produce the active compounds:

The wild type of the bacterium B. thuringiensis, which is pathogenic for insects, is a facultative anaerobe and is able to form endospores. It is distinguished from other spore-forming bacteria by forming during sporulation a parasporal protein crystal in the sporangium. The crystal protein acts as a stomach poison for insects and is called delta-endotoxin. The pathogenicity of B. thuringiensis essentially derives from the toxicity of the crystal protein; variants of B. thuringiensis which have lost the ability to form crystals have likewise lost their pathogenicity for insects.

The parasporal crystals are composed of glycoproteins with molecular weights of about 120,000. The protein molecules are covalently bonded together in the crystal by disulfide bridges. At neutral pH the crystals are insoluble in aqueous and organic solvents. In the alkaline pH range, above pH 9.0, they dissolve with the crystal protein being cleaved into smaller soluble peptides with molecular weights between about 23,000 and 70,000. .The peptides which are produced in this way include the active toxin.

The delta-endotoxins differ from other substances which are toxic for insects by being very toxic for sensitive insect larvae and having pronounced specificity, ie. not being toxic for other organisms, especially mammals. Their chemical structure leads to the expectation that they can undergo biodegradation without leaving residues.

These properties suggest the use of the delta-endotoxins as insecticides in crop protection. In fact, preparations based on B. thuringiensis have been available for some decades. The strains used for their preparation belong to the pathotype A. They are particularly used in fructiculture against certain species of butterfly larvae.

In 1977, isolates of B. thuringiensis and whose delta-endotoxins are toxic for diptera larvae which were subsequently called A 60 or Bacillus thuringiensis serovar. israelensis (BTI) were described.

Another name which is also used in the literature for the bacillus is B. cereus israelensis.

Attempts have been made in recent years to produce preparations which are based on such strains and are suitable for controlling mosquitos and blackflies (pathotype B).

However, problems arise when preparations based on strains of the pathotype B of B. thuringiensis are used: gnats breed on surface waters, into which it is necessary to introduce preparations based on B. thuringiensis serovar. israelensis. The introduction of viable spores into waters is impermissible for reasons of water protection because it entails the risk of the uncontrolled spread of microorganisms foreign to the water. Since every sporulating cell produces one spore and one protein crystal, the preparations which have hitherto been obtainable contain equal numbers of protein crystals and viable spores. On the experimental scale it is straightforward to separate spores and crystals. However, the methods used for this, such as density gradient centrifugation or two-phase separation, are impracticable on the industrial scale. It is possible by irradiation with UV or gamma rays to kill the spores without this entailing a reduction in the insecticidal activity of the crystal protein. However, sterilization of B. thuringiensis preparations by UV or gamma radiation is costly and thus cannot be justified economically.

Another problem is that the specific activity of the preparations obtained in this way is still too low. One of the causes of this, again, is that the preparations contain not only the protein crystals but also inactive spores, and in some cases vegetative cells also. This results in dilution, to a greater or lesser extent, of the actual active ingredient. Although sterilization of the crude preparation with gamma rays kills spores and vegetative cells they still remain as particles in the preparation. It is true that a certain dilution might be acceptable for some modes of use and application of the toxins. However, in practice, formulation of the toxins unavoidably results in dilution, eg. because weighting agents must be added or the preparations must be exposed to heat (for example during spray-drying).

The difficulties which have been described would be avoided if it were possible to develop, for the fermentation of strains of B. thuringiensis which are pathogenic for gnats, a process$ in which, from the outset, only protein crystals and no spores or vegetative cells are produced and which thus results in a highly concentrated preparation.

Published European Patent 99 301 described, inter alia, an asporous mutant of diptera-toxic Bacillus thuringiensis israelensis (or B. cereus ssp. israelensis, BCI) which has the strain name CB 3-104R and the deposition numbers 262 of the Canadian Committee on Culture Collections and ATCC 39 152 of the American Type Culture Collection.

Although this mutant is able to provide spore-free formulations of the crystalline toxin, this takes place only when all the individuals in the particular culture are always in the same stage of sporulation, because this mutant is not an asporous mutant in the true sense but is an organism which breaks down the endospore once the parasporal crystal has formed. The impossibility in practice of growing, on the industrial scale, cultures which contain organisms of the same age means that it is not possible with the mutant of published European Patent 99 301 to obtain spore- and cell-free preparations of the toxin directly, ie. without further measures.

However, European Patent A-99 301 contains much information on the phenomenology and practical processing of BTI, for which reason it can be used to supplement, where this appears necessary, the description which follows.

A publication which likewise deals with culturing asporous mutants of B. thuringiensis (serovar. kurstaki) is European Patent A-59 460 which may be referred to for supplementary information, as may the proposals to transfer the genetic information resulting in production of the toxin into a host organism (e.g. E. coli) which are contained in, for example, European Patent A-63 949.

We have found that a mutant, which is called HA-9 hereinafter, of the above mentioned B. thuringiensis A-60 or B. thuringiensis serovar. israelensis provides, under certain circumstances, toxin preparations which are free of spores and cell material, without a special sterilization step being required for this. The following should be stated beforehand:

DESCRIPTION OF THE PARENT STRAIN

In 1977 Goldberg and Margalit isolated, from a place where mosquitos bred in the Negev Desert in Israel, a bacillus having an insecticidal effect on mosquito larvae. This isolate was called A-60 and was identified as *B. thuringiensis* by de Barjac (C.R. Acad. Sci., Paris, Series D, 286 (1978), 797–800 and 1175–1178). Since it belongs to the hitherto unknown pathotype B and the flagellar serotype H-14, which was likewise new at that time, it is called *B. thuringiensis* serovar. *israelensis*. This strain forms the: starting material for the microorganism according to the invention.

In recent years further isolates belonging also to pathotype B but to flagellar serotypes H-8, H-10 and H-11 have been described. However, the specific toxicity of the crystal toxins from these isolates is lower than that of strain A-60.

For this reason, the strain A-60 was always used as the starting point for the mutants which are described hereinafter and those described according to the invention.

DESCRIPTION OF THE SPORULATION IN *B. THURINGIENSIS*

The production of endospores in bacilli generally commences in the stationary phase of growth. It may be regarded as a reaction to the fact that the substrates which can be utilized by the cell have become exhausted, and thus the living conditions have deteriorated. Vegetative cells are biochemically active, able to divide and sensitive to heat and desiccation. In contrast, endospores have a considerable resistance to heat and desiccation but are biochemically inactive and cannot divide. They represent a resting stage, which may persist for decades. It is terminated when the spore comes into contact with substrates which permit multiplication, eg. a nutrient solution in the laboratory. This entails the spore, in a process called germination, being converted into a vegetative cell. During spore formation, called sporulation hereinafter, considerable morphological changes take place in the sporulating cell. The description of sporulation is refined by dividing it into 7 stages which are commonly distinguished by roman numerals The formation of protein crystals starts in stage III.

Examination of the morphological changes during sporulation makes it clear that it entails a large number of consecutive processes. If the expression of one of the genes involved in sporulation is blocked by a mutation it often happens that the subsequent genes are likewise no longer expressed. For this reason, in many spo mutants sporulation stops at a particular stage. This property is used to characterize the mutation. Accordingly, a spo III mutant is blocked in stage III of sporulation, ie. sporulation comes to a halt in stage III. Sporulation in a spo VI mutant comes to a halt in stage VI, and a spo 0 mutant is unable to change from vegetative growth to sporulation. However, there are also exceptions. Thus, for example, the expression of the genes responsible for lysis of the sporangium in stage VII is unaffected by the incompetence of spo III or spo V genes. As previously mentioned, synthesis of the crystals has started in stage III. Thus, a defect in a gene required in stage III or thereafter ought not to affect the syntesis of crystals but ought to affect the production of an intact heat-resistant spore.

ISOLATION OF SPO MUTANTS

Colonies of *B. thuringiensis* on nutrient agar undergo considerable changes over a period of some days. Starting in the center, the initially brownish colonies become cloudy and white. Occasionally, when the colonies are very large, the center of the colony collapses and a type of crater is formed. These changes in the colony morphology are brought about by sporulation. Cells in the center of a colony are the first to experience a shortage of substrates and thus they are the first to begin changing their metabolism over to sporulation. Hence, a practiced microbiologist who is familiar with the organism is easily able to recognize whether a colony is sporulating. *B. thuringiensis* reaches this stage after 3 or 4 days at 28° C. Colonies of mutants which are no longer able to sporulate do not become cloudy but become somewhat more translucent in places. It is possible by this means after mutagenesis, eg. with NTG, to examine thousands of individual colonies without excessive expenditure of time.

Not all the colonies with a changed morphology are spo mutants. For this reason, for further characterization samples are take from each changed colony and examined under the phase-contrast microscope It is then easy to see whether the colonies are spo mutants and whether protein crystals are still being produced Growth and sporulation in a colony of *B. thuringiensis* are not synchronized, ie. when sporulation is complete in the center of a colony the cells on its edge are still in the state of vegetative growth. For this reason it is still possible to propagate a mutant further even if the genetic defect in sporulation results in destruction of the ripening spore.

Many asporogenic mutants of the strain A-60 and of *B. thuringiensis* have been isolated in this manner. Many of them have a high rate of reversion back to the parent sporogenic strain. Only the two mutants HA-1 and HA-5 have been used for further development because no reversion to the parent sporogenic strain has been observed with them.

DESCRIPTION OF THE PROPERTIES OF SPO MUTANTS

STRAIN HA-1

The first asporogenic mutant of the strain A-60 which underwent detailed examination is called strain HA-1. A sporulated culture of this mutant differs from a corresponding culture of the strain A-60 in that relatively large oval cells covered by an exosporium are seen in place of the refractive endospores. Both cultures contain the parasporal crystals of irregular shape which are typical of strains pathogenic for gnats.

The appearance of an insecticidal effect and heat-stable or -labile endospores during fermentation of the strain A-60 and the mutant HA-1 can likewise be followed visually; it :merges that the mutant grows at the same rate as the parent strain; the development of toxicity also takes place synchronously. However, there is no formation of heat-resistant spores by the mutant.

The picture under the electron microscope shows that the cells which have been described are defective spores since they contain all the layers of the wall typical of spores. The defective spores differ from the intact ones in that the cytoplasm is not condensed, and they are not resistant to heat. The spore cortex is not, as it is in the strain A-60, a uniformly thick layer which entirely covers the spore, but appears to have gaps and to cover the spore incompletely.

The spore cortex is formed in stage V of sporulation. Since the mutant still has a visible but defective spore cortex, without condensation of the cytoplasm, it is called a spo V mutant. Although the defect is located in a stage V gene the lysis of the sporangium which is typical of stage VII takes place. Expression of the genes required for this appears to be unaffected by the spo V mutation.

The heat-labile, defective spores can be inactivated at the end of a fermentation by heating at 80° C. for 10 minutes without diminishing the toxicity of the protein crystals. Thus it is possible without irradiation to obtain a crude product which complies with the requirements of water protection.

THE STRAIN HA-5 ACCORDING TO THE INVENTION

The mutant HA-1 has the disadvantage that the crude product contains not only the protein crystals but also defective spores which cause a considerable dilution of the active ingredient. For this reason, further mutants defective in an earlier stage of sporulation were sought. During further examination of apparently suitable colonies a mutant called HA-5 was isolated. HA-5 is deposited in the German Collection of Microorganisms, Federal Republic of Germany, under deposit No. DSM 3439. As can be seen under the microscope, lysis of the sporangium also takes place with this mutant, with only the typical protein crystals, and no spores, being released. For more detailed characterization, this mutant was fermented and samples were taken at various times after the end of logarithmic growth, and ultra thin sections of the sporulating cells were examined under the electron microscope. The prespore represents the most advanced stage of sporulation observable in the mutant HA-5. The double membrane and, between the layers, the primary cell wall of the spore are seen. This corresponds to the state of development of the spore in stage III. This mutant is thus called a spo III mutant. The primary cell wall of the spore has the same structure as the cell wall of the sporangium This explains why enzymes able to lyse the sporangium also break down the prespore, so that only protein crystals remain at the end of a fermentation.

PREPARATION OF TS MUTANTS

Deficiencies of the Spo Mutants

It is observed with many bacillus strains that not all the cells sporulate at the end of logarithmic growth. The proportion of sporulating cells in a culture in the stationary phase may fall to below 1%. Strains of this type are called oligosporogenic. The determining causes of this phenomenon may be genetic, and very often the composition of the medium also contributes. With strain A-60, too, vegetative cells are still visible in cultures in stage VII of sporulation.

The following phenomenon occurs on fermentation of the mutant HA-5. At the end of the logarithmic phase of growth the nutrient medium is exhausted and the cells stop growing. The overwhelming majority of the cells change their metabolism over to sporulation, and the remaining cells rest. At the end of sporulation the sporangia and prespores are lysed. This results in release into the medium of cell constituents which are suitable as substrates, whereupon the vegetative cells which are still present start to grow again. The increase in the number of vegetative cells causes the concentration of protein crystals in the crude product to decrease; since the vegetative cells are very much larger than protein crystals the dilution effect is very pronounced even with a small increase in vegetative cells. It is possible when fermenting the mutant HA-5 to restrict secondary growth by choosing the correct time of harvesting, but this requires frequent sampling and careful monitoring towards the end of the fermentation. Even so, crude preparations which have been produced using the mutant HA-5 still contain vegetative cells.

Description of the strain HA-9 according to the invention

*B. thuringiensis* grows at from about 25 to 45° C. There is one type of mutants called temperature-sensitive, abbreviated to ts mutants. Mutations of this type may occur in a variety of genes. They result in, for example, the cell synthesizing an intact gene product at 28° C. and a defective gene product at 43° C.

In order to prevent secondary growth in the asporogenic mutant HA-5 at the end of sporulation it was treated once again with NTG, and those of the surviving cells which have a ts defect in vegetative growth were selected. All the mutants which were isolated grow below 30, eg. at 28° C., but not above 35, eg. at 43° C., and still have the spo III mutation. When the mutants are allowed to grow, eg. at 28° C., until sporulation has started, and then the temperature is increased to, for example, 43° C. there is no impairment of crystal synthesis. Among the mutants fulfilling these conditions are some which exhibit an additional effect. When the temperature is increased to 43° C. there is not only cessation of growth but also onset of lysis of vegetative cells, so that there is a rapid decrease in their numbers.

This effect is particularly marked in the mutant HA-9. HA-9 is deposited in the German Collection of Microorganisms, Federal Republic of Germany, under deposit No. DSM 3440. When the temperature is increased to 43° C. during sporulation of this mutant all the vegetative cells in the culture lyse within a few hours. The biomass obtained by centrifugation of the culture medium contains neither spores nor vegetative cells and contains almost exclusively protein crystals.

EXAMPLE

Description of the Process for the Preparation of Protein Crystals Which are Toxic for Gnats by Use of the Mutant HA-9

A fermentation medium containing soybean meal, yeast autolysate, potato starch and mineral salts has been developed. The composition of the medium is shown in the table.

Two 500 ml flasks each with a baffle and each containing 250 ml of fermentation medium were inoculated with the mutant HA-9. The flasks were then shaken at 28° C. for 16 h. The colony used for inoculation of the flasks had been grown on yeast extract/glucose/peptone agar at 28° C. and was not more than 48 h old.

The overnight cultures were used to inoculate a 25 l fermenter containing fermentation medium equilibrated at 28° C. Tumble fermenters were used for this. The speed of the agitator was set at 1,200 rpm, and the aeration was controlled at 25 l/min.

After 7 h the cells in the prefermenter were in the middle to late logarithmic phase of growth and were used to inoculate the main fermenter. This entailed the contents of the prefermenter being pumped into the main fermenter which contained 200 l of sterilized fermentation medium equilibrated at 28° C. The speed of the turbine was controlled at 1,200 rpm and the aeration was controlled at 6 m$^3$/h. Since the medium becomes very acid in the logarithmic phase of growth the pH was maintained at 7.4 by pumping in 2 N NaOH. Towards the end of the logarithmic phase of growth the Ph in the culture rises above 8.0. Once the synthesis of the protein crystals had been initiated the temperature in the fermenter was raised to 43° C. after 19 h. After a total of 26 h the fermentation was stopped, and the protein crystals were harvested by centrifugation.

TABLE

| | |
|---|---|
| Soybean meal, defatted | 10.0 g/l |
| Potato starch | 5.0 g/l |
| Yeast autolysate | 2.0 g/l |
| K$_2$HOP$_4$, anhydrous | 1.0 g/l |
| MgSO$_4$ × 7 H$_2$O | 0.3 g/l |
| CaCl$_2$ × 6 H$_2$O | 0.08 g/l |
| MnCl$_2$ × 4H$_2$O | 0.05 g/l |
| CuCl | 0.005 g/l |
| ZnCl$_2$ | 0.005 g/l |
| FeCl$_3$ | 0.005 g/l |

For use as an insecticide, the preparation having insecticidal activity, or toxin, obtained according to the invention is mixed in a conventional manner with customary additives (vehicles, adhesion promoters, wetting agents, etc.) and converted into a suitable form for use. The insecticide formulated in this way can be used in the form of a wettable powder or a suspension or as granules or the like.

Use example *AEDES AEGYPTI, Yellow-fever Mosquito*

Type of test:
Continuous contact/feeding; *Ades aegypti*
Test procedure:

200 ml of tap water at about 23° C. are introduced into plastic beakers of capacity 250 ml and diameter 8 cm, and 20 Aedes larvae in the second larval stage are added. The test substance in the form of an aqueous emulsion or suspension is then added to the vessel and, after 24 hours, the mortality in the vessel is determined, and the LC$_{50}$ is calculated.

| | LC$_{50}$ (ppm) after 24 h | |
|---|---|---|
| | Crude product | Freeze-dried |
| Wild type | 0.15 | 0.018 |
| HA5 | 0.030 | 0.0065 |
| HA9 | 0.032 | 0.009 |

We claim:

1. *Bacillus thuringiensis* serovar. *israelensis* SM 3439.
2. *Bacillus thruingiensis* serovar. *israelensis* SM 3440.
3. A strain of Bacillus having all the identifying ZAEHNER et al., Ser No. 022,830 characteristics of *Bacillus thruingiensis* serovar. *israelensis* SM 3439.
4. A strain of Bacillus having all the identifying characteristics of *Bacillus thuringiensis* serovar. *israelensis* SM 3440.

* * * * *

UNITED STATES PATENT AND TRADEMARK OFFICE
CERTIFICATE OF CORRECTION

PATENT NO. : 4,996,156

DATED : February 26, 1991

INVENTOR(S) : Hans Zaehner, et al.

It is certified that error appears in the above-identified patent and that said Letters Patent is hereby corrected as shown below:

Column 8:

Claims 1, 2, and 4: "SM" should read --DSM--

Claim 2: "thruingiensis" should read --thuringiensis--

Claim 3: should read --A strain of Bacillus having all the identifying characteristics of Bacillus thuringiensis serovar. israelensis DSM 3439--

Signed and Sealed this

Tenth Day of November, 1992

Attest:

DOUGLAS B. COMER

Attesting Officer

Acting Commissioner of Patents and Trademarks